United States Patent
Miyazaki et al.

(10) Patent No.: US 9,758,846 B2
(45) Date of Patent: Sep. 12, 2017

(54) SUPER ELASTIC ZIRCONIUM ALLOY FOR BIOLOGICAL USE, MEDICAL INSTRUMENT AND GLASSES

(75) Inventors: Shuichi Miyazaki, Tsukuba (JP); Heeyoung Kim, Tsukuba (JP); Yosuke Sato, Tsukuba (JP)

(73) Assignee: University of Tsukuba, Ibaraki (JP)

( * ) Notice: Subject to any disclaimer, the term of this patent is extended or adjusted under 35 U.S.C. 154(b) by 514 days.

(21) Appl. No.: 14/342,549

(22) PCT Filed: Aug. 28, 2012

(86) PCT No.: PCT/JP2012/005387
§ 371 (c)(1),
(2), (4) Date: Apr. 22, 2014

(87) PCT Pub. No.: WO2013/035269
PCT Pub. Date: Mar. 14, 2013

(65) Prior Publication Data
US 2014/0271335 A1  Sep. 18, 2014

(30) Foreign Application Priority Data

Sep. 5, 2011 (JP) ................................ 2011-192977

(51) Int. Cl.
*C22C 14/00* (2006.01)
*C22C 16/00* (2006.01)
(Continued)

(52) U.S. Cl.
CPC .............. *C22C 14/00* (2013.01); *A61L 27/06* (2013.01); *A61L 27/50* (2013.01); *A61L 29/02* (2013.01); *A61L 29/14* (2013.01); *A61L 31/022* (2013.01); *A61L 31/14* (2013.01); *C22C 16/00* (2013.01); *C22C 30/00* (2013.01); *C22C 30/04* (2013.01); *C22F 1/186* (2013.01); *G02C 5/008* (2013.01); *A61C 2201/007* (2013.01);
(Continued)

(58) Field of Classification Search
CPC ................................ C22C 14/00; C22C 16/00
USPC .......................................................... 420/417
IPC ......................................... C22C 1/0491,45/10
See application file for complete search history.

(56) References Cited

U.S. PATENT DOCUMENTS 6,767,418 B1 * 7/2004 Zhang .................... A61L 27/06
148/421
6,786,984 B1    9/2004 Hanada et al.
(Continued)

FOREIGN PATENT DOCUMENTS

JP       2006089825 A      4/2006

OTHER PUBLICATIONS

PCT/JP2012/005387 International File Date: Aug. 28, 2012—International Search Report; University of Tsukuba; 2 pages.

*Primary Examiner* — Weiping Zhu
(74) *Attorney, Agent, or Firm* — Sunstone IP

(57) ABSTRACT

Provided is a super elastic alloy for biological use having a high biocompatibility, good processability and super elasticity, said super elastic alloy being a super elastic zirconium alloy for biological use comprising 27-54 mol % inclusive of titanium, 5-9 mol % inclusive of niobium which is a β phase-stabilizing element capable of stabilizing the β phase of zirconium, and 1-4 mol % inclusive in total of tin and/or aluminum which are ω phase-suppressing elements capable of suppressing the ω phase of zirconium, with the balance consisting of zirconium and inevitable impurities.

4 Claims, 1 Drawing Sheet

(51) Int. Cl.
*C22F 1/18* (2006.01)
*A61L 27/06* (2006.01)
*A61L 27/50* (2006.01)
*A61L 29/02* (2006.01)
*A61L 29/14* (2006.01)
*A61L 31/02* (2006.01)
*A61L 31/14* (2006.01)
*C22C 30/00* (2006.01)
*C22C 30/04* (2006.01)
*G02C 5/00* (2006.01)

(52) U.S. Cl.
CPC ....... *A61L 2400/16* (2013.01); *A61L 2430/02* (2013.01); *A61L 2430/12* (2013.01); *A61L 2430/24* (2013.01)

(56) References Cited

U.S. PATENT DOCUMENTS

| | | |
|---|---|---|
| 2002/0033717 A1 | 3/2002 | Matsuo |
| 2003/0188810 A1 | 10/2003 | Tanaka et al. |
| 2005/0254990 A1 | 11/2005 | Tanaka et al. |
| 2010/0073624 A1 | 3/2010 | Wang et al. |
| 2011/0070121 A1 | 3/2011 | Lee et al. |

* cited by examiner

SUPER ELASTIC ZIRCONIUM ALLOY FOR BIOLOGICAL USE, MEDICAL INSTRUMENT AND GLASSES

CROSS-REFERENCE TO RELATED APPLICATIONS

This application claims priority to PCT Application No. PCT/JP2012/005387, having a filing date of Aug. 28, 2012, the entire contents of which are hereby incorporated by reference.

FIELD OF TECHNOLOGY

The present invention relates to a super-elastic zirconium alloy for living tissues, and medical appliance and eyeglasses that utilize the super-elastic zirconium alloy for living tissues.

BACKGROUND

A variety of alloys for living tissues are used in surgeries and implants in the medical field.
For example, Ti—Ni alloys have advantages such as high strength, wear resistance, corrosion resistance, and high compatibility with living tissues, etc., and are used as materials for living tissues in various medical appliances.

However, Ti—Ni light alloys have poor processability and their cold processing rate is limited, usually within a range of 30%~40%; therefore, additional processing procedures such as intermediate annealing are required. Consequently, these alloys require high processing cost, and their application in products with complex shapes is limited. Moreover, in Ti—Ni alloy materials for living tissues, the Ni element may cause allergy symptoms. Therefore, researches have been made to develop materials for living tissues that are more safer without using the elements that may cause toxic or allergic risks to living tissues.

With respect to such materials for living tissues, the techniques described in the following patent documents 1~4 are known.

In FIG. 3 of patent document 1 (Japanese Patent Document JP3521253), a Ti—Nb—Sn shape memory alloy for living tissues, composed of niobium within a range of 10 at %~20 at %, tin within a range of 3 at %~8 at %, and titanium that accounts for the remaining portion (74 at %~86 at %), is disclosed. In the technique disclosed in patent document 1, as illustrated by the stress-strain curve shown in FIG. 10, the maximum recoverable strain (maximum strain—residual strain after unloading) has an elasticity of 3.5% only.

In patent document 2 (Japanese Patent Document JP3884316), a Ti—Mo—Ga super-elastic titanium alloy for living tissues, composed of molybdenum (Mo) within a range of 2 at %~12 at %, gallium (Ga) less than 14 at %, and titanium (Ti) that accounts for the remaining portion, and a Ti—Mo—Ge super-elastic titanium alloy for living tissues, composed of molybdenum within a range of 2 at %~12 at %, germanium (Ge) less than 8 at %, and titanium that accounts for the remaining portion, are disclosed.

In patent document 3 (Japanese Patent Document JP4128975), a Ti—Nb—(Au, Pt, Pd, Ag) super-elastic titanium alloy for living tissues is disclosed, and the composition of the alloy is as follows: the amount of niobium is within a range of 5 mol %~40 mol %, the amounts of Au, Pt, Pd and Ag are lower than 10 mol % respectively and the total amount of Au, Pt, Pd and Ag is lower than 20 mol %, and titanium accounts for the remaining portion.

In patent document 4 (Japanese Patent Document JP4302604), a Ti—(Ta, Nb)—Zr—Mo super-elastic titanium alloy for living tissues is disclosed, and the composition of the alloy is as follows: the amount of tantalum (Ta) is x mol %, the amount of niobium (Nb) is y mol %, and 15 mol≤1.5x+y≤45 mol %, the amount of zirconium (Zr) is within a range of 1 mol %~20 mol %, the amount of molybdenum (Mo) is within a range of 1~6 mol %, and the total amount of Ta, Nb, Zr, and Mo is lower than 60 mol %, and titanium account for the remaining portion. In addition, in patent document 4, as illustrated by the stress-strain curve shown in FIG. 2 and FIG. 3, the elasticity is up to 4%.

SUMMARY

Problems to be Solved (Problems in the Prior Art)
In the super-elastic titanium alloys disclosed in patent documents 1 and 4, the elasticity is only up to 5%. Therefore, it is difficult to use those alloys for parts that require high elasticity, such as stents used in angioplasty operations.

In addition, in the technical schemes disclosed in patent documents 1~4, the alloys do not have enough super-elasticity or cold processability.

Moreover, in the technical scheme disclosed in patent document 3, noble metal elements (Au, Pt and Ag etc.) are used; therefore, the cost is very high.

The object of the present invention is to provide a super-elastic alloy for living tissues, which has high compatibility with living tissues, good processability, and super-elasticity.

Technical Solution to the Problems

To solve the technical problems described above, the super-elastic zirconium alloy for living tissues as described in claim 1 is characterized in: the super-elastic zirconium alloy for living tissues comprises the following constituents:
titanium within a range of 27 mol %~54 mol %;
niobium within a range of 5 mol %~9 mol %, serving as a β phase stabilizing element for stabilizing the β phase of zirconium (Zr);
at least one of tin and aluminum within a range of 1 mol %~4 mol %, serving as a ω phase inhibiting element for inhibiting the ω phase of zirconium (Zr);
zirconium (Zr), which accounts for the remaining portion;
inevitable impurities.

To solve the technical problems described above, the medical appliance as described in claim 2 is characterized in that the medical appliance is made of the super-elastic zirconium alloy for living tissues according to claim 1.

To solve the technical problems described above, the eyeglasses as described in claim 3 is characterized in that the eyeglasses has an eyeglass frame, which is made of the super-elastic zirconium alloy for living tissues according to claim 1.

Beneficial Effects of the Invention

In a technical scheme according to claim 1, the present invention provides a super-elastic zirconium alloy for living tissues, which has high compatibility with living tissues, good processability and super-elasticity.

In a technical scheme according to claim 2, the present invention provides a medical appliance, which is made of the super-elastic zirconium alloy for living tissues that has high compatibility with living tissues, good processability and super-elasticity.

In a technical scheme according to claim 3, the present invention provides an eyeglasses, which is made of the super-elastic zirconium alloy for living tissues that has high compatibility with living tissues, good processability and super-elasticity.

BRIEF DESCRIPTION

DETAILED DESCRIPTION

Figure 1:
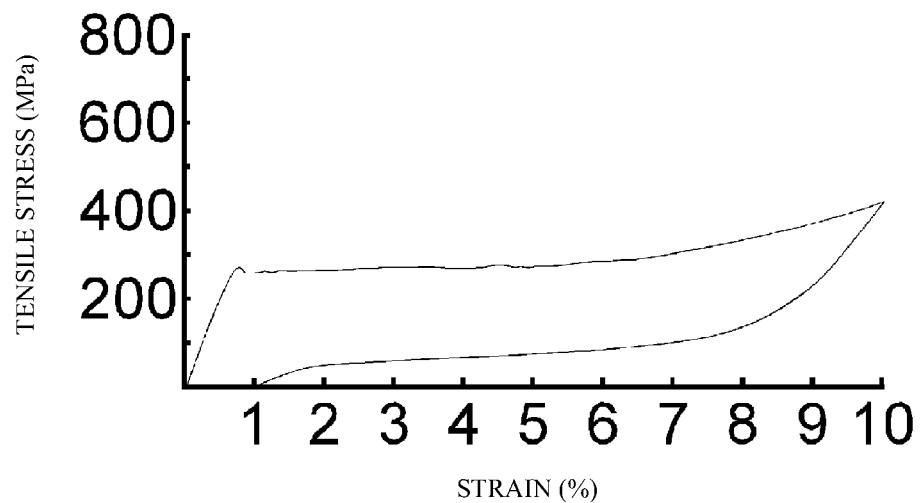
FIG. 1 shows a stress-strain curve of the alloy 5 in an example of the present invention at room temperature.

Here under the present invention will be detailed in embodiments. However, the present invention is not limited to the following embodiments.

The alloy in the present invention is a zirconium alloy in which zirconium (Zr) is the principal element. In addition, the alloy in the present invention has a function of decreasing the temperature of transition from β phase (the parent phase of martensite transition of Zr at room temperature) to α phase, which is to say, the alloy contains titanium (Ti) and niobium (Nb) that serve as β phase stabilizing elements for stabilizing the β phase of Zr, and the alloy has thermo-elastic martensite transition.

Moreover, Ti and Nb are dissolved in Zr, and thereby play a dissolution enhancing role, i.e., they increase the critical stress of sliding deformation, and thereby inhibit sliding deformation and are helpful for attaining super-elasticity. Furthermore, with respect to Ti, since the variability of transition temperature that causes relative component variations is decreased, the transition temperature can be controlled easily, and stability can be attained.

In addition, since the alloy in the present invention contains at least one of tin (Sn) and aluminum (Al) that serve as a ω phase inhibiting element for inhibiting the ω phase of Zr, the super-elasticity is improved by inhibiting the ω phase that is an embrittling phase of Zr or by α phase precipitation hardening.

Hereunder the present invention will be detailed in embodiments.

(Preparing Method of the Alloy)

Here, alloys 1~13 and 21~26, which are used as embodiments of the present invention, and alloys 14~20 and alloy 27, which are used as comparative examples, are produced as follows. The alloying constituents of these alloys are shown in Table 1. For test pieces to be used in experiments, the mol % values of each metallic element is calculated, and the metallic elements are melted in a non-consumable electrode argon arc smelting furnace, to produce alloy ingots. Namely, alloy 1 (Zr—54Ti—9Nb—2Sn) is an alloy composed of the following alloying constituents: 54 mol % of Ti, 9 mol % of Nb, 2 mol % of Sn, and Zr that accounts for the remaining portion (35 mol %).

(Assessment Method of Cold-processability)

Next, the obtained ingots are processed by cold rolling, till the ingots are fractured. The cold-processability of the alloys is assessed by their maximum cold processing rate. The test samples are in a thickness of 10 mm before rolling, and the percent of reduction per rolling cycle in the cold rolling process is 5%.

If the maximum processing rate is higher than 80% without intermediate annealing, the cold-processability is deemed as excellent and ranked as "○"; if the maximum processability rate is higher than 80% with intermediate annealing (at 800° C., for 10 minutes.) in the rolling process, the cold-processability is deemed as good and ranked as "Δ"; otherwise the cold-processability is ranked as "×".

(Assessment Method of Super-elasticity)

For super-elasticity assessment, the following tensile test is carried out for the cold-rolled test samples, wherein, test samples that pre-heat-treated at 800° C. for 30 minutes are tensioned to strain 2.0%, 2.5%, 3.0%, . . . , with 0.5% strain increment per cycle. In addition, a loading-unloading cycle is repeated before the maximum recoverable strain is reached or the test sample fractures, to access the test samples by their maximum recoverable strain. Moreover, the Young's modulus value of each alloy is measured. The alloys 1~13 and 21~16, which are used as embodiments of the Zr—Ti—Nb—(Sn, Al) alloy, and alloys 14~20 and alloy 27, which are used as comparative examples, are listed in Tables 1 and 2.

(Assessment Method of Super-elasticity)

TABLE 1

| Category | Alloy No. | Ti | Nb | Sn | Zr | Maximum Recoverable Strain (%) | Young's Modulus (GPa) | Processability |
|---|---|---|---|---|---|---|---|---|
| Examples | 1 | 54.0 | 9.0 | 2.0 | Remaining portion | 7.1 | 40 | ○ |
| | 2 | 54.0 | 8.0 | 3.0 | Remaining portion | 7.0 | 42 | ○ |
| | 3 | 54.0 | 7.0 | 4.0 | Remaining portion | 6.7 | 43 | ○ |
| | 4 | 44.5 | 8.5 | 1.0 | Remaining portion | 7.9 | 47 | ○ |
| | 5 | 45.0 | 8.0 | 2.0 | Remaining portion | 8.9 | 45 | ○ |
| | 6 | 45.0 | 7.0 | 3.0 | Remaining portion | 8.7 | 44 | ○ |
| | 7 | 45.0 | 6.0 | 4.0 | Remaining portion | 6.4 | 42 | ○ |
| | 8 | 45.5 | 5.0 | 4.0 | Remaining portion | 5.1 | 41 | Δ |
| | 9 | 36.0 | 8.0 | 2.0 | Remaining portion | 7.9 | 38 | ○ |

TABLE 1-continued

| Category | Alloy No. | Ti | Nb | Sn | Zr | Maximum Recoverable Strain (%) | Young's Modulus (GPa) | Processability |
|---|---|---|---|---|---|---|---|---|
| | 10 | 36.0 | 7.0 | 3.0 | Remaining portion | 7.8 | 41 | ○ |
| | 11 | 36.0 | 6.0 | 4.0 | Remaining portion | 6.2 | 43 | Δ |
| | 12 | 27.0 | 8.0 | 2.0 | Remaining portion | 7.3 | 42 | ○ |
| | 13 | 27.0 | 7.0 | 3.0 | Remaining portion | 7.0 | 45 | Δ |
| Comparative Examples | 14 | 62.0 | 9.0 | 2.0 | Remaining portion | 1.6 | 52 | ○ |
| | 15 | 54.0 | 10.0 | 2.0 | Remaining portion | 1.8 | 38 | ○ |
| | 16 | 45.0 | 8.0 | 0.0 | Remaining portion | 1.4 | 54 | ○ |
| | 17 | 45.0 | 5.0 | 6.0 | Remaining portion | — | | x |
| | 18 | 45.0 | 4.0 | 2.0 | Remaining portion | — | | x |
| | 19 | 27.0 | 4.0 | 2.0 | Remaining portion | — | | x |
| | 20 | 0.0 | 8.0 | 2.0 | Remaining portion | 1.8 | 62 | Δ |

TABLE 2

| Category | Alloy No. | Ti | Nb | Sn | Al | Zr | Maximum Recoverable Strain (%) | Young's Modulus (GPa) | Processability |
|---|---|---|---|---|---|---|---|---|---|
| Examples | 21 | 45.0 | 6.0 | 3.0 | 1.0 | Remaining portion | 6.3 | 44 | ○ |
| | 22 | 45.0 | 6.0 | 2.0 | 2.0 | Remaining portion | 6.1 | 43 | ○ |
| | 23 | 45.0 | 6.0 | 1.0 | 3.0 | Remaining portion | 5.8 | 46 | ○ |
| | 24 | 45.0 | 6.0 | 0 | 4.0 | Remaining portion | 5.5 | 48 | ○ |
| | 25 | 45.0 | 7.0 | 2.0 | 2.0 | Remaining portion | 7.7 | 49 | ○ |
| | 26 | 27.0 | 8.0 | 0 | 2.0 | Remaining portion | 6.5 | 48 | ○ |
| Comparative Example | 27 | 45.0 | 6.0 | 0 | 8.0 | Remaining portion | — | — | x |

FIG. 1 shows a stress-strain curve of the alloy 5 in an example of the present invention at room temperature.

Figure 2:
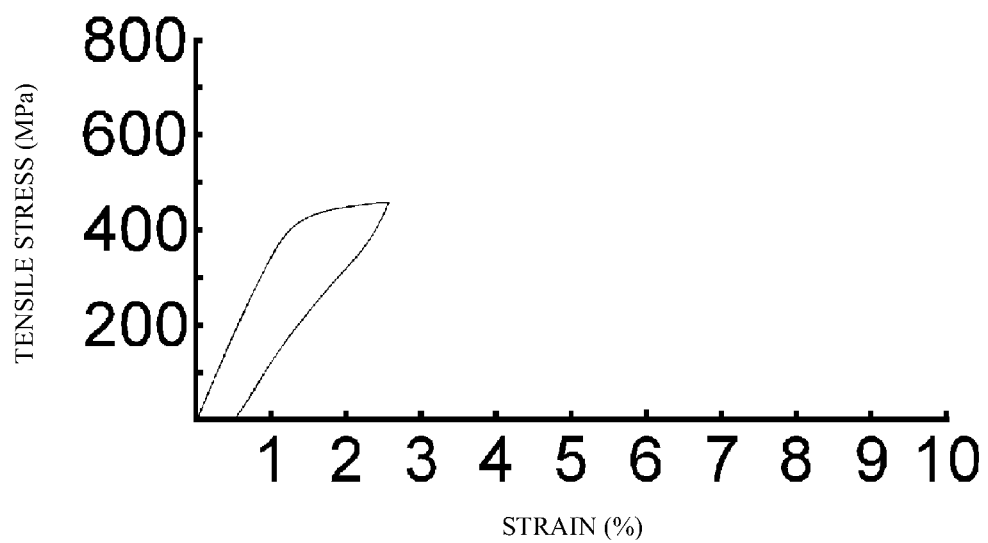
FIG. 2 shows a stress-strain curve of the alloy 15 in a comparative example at room temperature.

FIG. 2 shows a stress-strain curve of the alloy 15 in a comparative example at room temperature.

In FIG. 1 and FIG. 2, the stress-strain curves of alloy 5 and alloy 15 are illustrated as examples. As shown in FIG. 1, for alloy 5, the strain recovers from 10% to 1.1%, i.e., the maximum recoverable strain is 8.9%; therefore, the alloy 5 is deemed as having excellent super-elasticity.

As shown in FIG. 2, for alloy 15, the strain recovers from 2.5% to 0.6%, i.e., the maximum recoverable strain is 1.9% only; therefore, the alloy 15 is deemed as having poor super-elasticity.

According to the above test results, the alloys 1~13 and 21~26, which represent the Zr—Ti—Nb—(Sn, Al) zirconium alloy that contains Ti within a range of 27 mol %~54 mol %; Nb within a range of 5 mol %~9 mol %, which serves as a β phase stabilizing element; Sn and Al within a range of 1 mol %~4 mol %, which serve as ω phase inhibiting elements; and Zr, which accounts for the remaining portion, have high cold processability and super-elasticity, whose maximum recoverable strain is higher than 5.0%. Especially, except for alloys 8, 23 and 24, alloys 1~7, 9~13, 21, 22, 25 and 26 have good super-elasticity, with maximum recoverable strain higher than 6.0%, and alloys 5 and 6 have excellent super-elasticity, with maximum recoverable strain close to 9.0%. In Table 1 and Table 2, in alloy 14 in which the amount of Ti is higher than 54 mol % or in alloy 20 in which the amount of Ti is lower than 27 mol %, it is confirmed that the super-elasticity is degraded or even no super-elasticity is found. Accordingly, among alloys 1~13, 21~26, and alloys 14 and 20, it is confirmed that the super-elasticity is degraded or even no super-elasticity is found if the amount of Ti is beyond the range of 27 mol %~54 mol %.

In addition, in Table 1, in alloy 15 in which the amount of Nb is higher than 9 mol % or in alloys 18 and 19 in which the amount of Nb is lower than 5 mol %, it is confirmed that the super-elasticity is degraded or even no super-elasticity is found; especially, in alloys 18 and 19 in which the amount of Nb is lower than 5 mol %, it is confirmed that the cold processability is also degraded. Accordingly, among alloys 1~13, 21~26 and alloys 15, 18 and 19, it is confirmed that the processability will be degraded if the amount of Nb is lower than 5 mol % and the super-elasticity is degraded or even on super-elasticity is found if the amount of Nb is higher than 9 mol %. Moreover, in Tables 1 and 2, in alloy 16 in which the total amount of Sn and Al is lower than 1 mol % or in alloys 17 and 27 in which the total amount of Sn and Al is higher than 4 mol %, it is confirmed that the super-elasticity is degraded or even no super-elasticity is found; especially, in alloys 17 and 27 in which the total amount of Sn and Al is higher than 4 mol %, it is confirmed that the cold processability is also degraded. Accordingly, in alloys 1~13, 21~26 and alloys 16, 17 and 27, it is confirmed that no super-elasticity is found or the super-elasticity is degraded if the total amount of Sn and Al is lower than 1 mol %, owing to the effect of ω phase that serves as an embrittling phase, and the processability is degraded if the total amount of Sn and Al is higher than 4 mol %.

Furthermore, the alloys 1~13 and 21~26 do not contain Ni that may cause an allergic risk. As described in FIG. 1 and FIG. 2 of Patent Document 1, the alloys are composed of Zr, Ti, Nb and Sn, which are highly compatible with living tissues, and will not cause allergic symptoms.

In addition, compared with existing Ti—Ni alloys and high-elasticity Ti alloys, the alloy disclosed in the present invention contains great amount of Zr, which has a greater atomic number. Usually, the greater the atomic number of an element is, the higher the X-ray absorptivity of the element will be. Therefore, compared with existing alloys, the alloy disclosed in the present invention has an excellent X-ray angiographic feature. For example, the alloy disclosed in the present invention can be implanted as an artificial implant into living tissues of a patient. After the operation, when the patient receives radiographic inspection (i.e., in the case of so-called X-ray angiography), the X-ray angiogram of the implant can be reflected more clearly when compared with the X-ray angiograms of implants made of existing alloys.

Moreover, compared with existing Ti—Ni alloys or high-elasticity Ti-based alloys, the alloys disclosed in the present invention contain a great amount of Zr, which has a low magnetic susceptibility; therefore, the overall magnetic susceptibility of the entire alloys is low. In Magnetic Resonance Imaging (MRI) apparatuses that are widely applied in the medical field in recent years, the MRI image will be disordered if there is any metal device existing in the patient's body. That phenomenon is referred to as a MRI artefact. A MRI artefact will be created under metal magnetization effect in the MRI magnetic field.

To suppress MRI artefacts, metal materials with low magnetic susceptibility are desirable. Especially, in MRI apparatuses that were developed recently, it is highly necessarily to reduce MRI artefacts, because these apparatuses employ a stronger magnetic field. To that end, compared with existing alloys, the alloy disclosed in the present invention is expected to achieve an effect of reduced magnetic susceptibility and reduced MRI artefacts.

In addition, the alloys disclosed in the present invention have a Young's modulus within a range of 38~49 GPa, as shown in Tables 1 and 2. The Young's modulus of human bones is within a range of 10~40 GPa. In contrast, the Young's modulus of ordinary stainless steel is 200 GPa, and the Young's modulus of high-elasticity Ti-based alloys is 100 GPa. Compared with existing alloys, the alloys disclosed in the present invention have a Young's modulus closer to the Young's modulus of human bones; therefore, the alloys disclosed in the present invention are ideal bone substitution materials that can avoid allergy.

INDUSTRIAL APPLICATIONS

Since the zirconium alloys disclosed in the present invention are super-elastic zirconium alloys for living tissues that have high compatibility with living tissues, super-elasticity, and good cold processability, preferably they are used for living articles that directly contact with medical appliances or skin. Preferably the alloys are used for medical appliances for living tissues, such as metal guiding wires for tubes in medical operations, metal wires for orthodontics, medical stents that are inserted into tubular parts in human body such as blood vessels, tracheae, alimentary tracts to attain an internal expansion purpose, or actuators of endoscopes.

In addition, as living articles that contact with skin, preferably the alloys are used as eyeglass frames, nose pads, frames for watch, straps, buckles, wrist bands, pearls, necklaces, ear rings, and shoelace buckles, etc.

Moreover, with its high compatibility with living tissues, favorable X-ray angiographic feature, and good MRI artefact prevention feature, preferably the alloys are used for hard tissue substitution medical appliances, such as artificial bones, artificial joints, and artificial tooth roots, etc. In addition, the alloy can also be used for medical appliances for implants or permanent connectors such as bone plates, screws, bolts, wires, clips, nails, intramedullary nail, etc. That is to say, the alloys disclosed in the present invention can also be used for medical appliances such as implants in human bodies for medical purpose.

The invention claimed is:

1. A super-elastic zirconium alloy having thermos-elastic martensite transition for living tissues comprising:
    titanium within a range of 27 mol %~54 mol %;
    niobium within a range of 5 mol %~9 mol %, serving as a β phase stabilizing element for stabilizing the β phase of zirconium;
    at least one of tin and aluminum within a range of 1 mol %~4 mol %, serving as a ω phase inhibiting element for inhibiting the ω phase of zirconium;
    zirconium, which accounts for the remaining portion; and inevitable impurities.

2. A medical appliance, made of the super-elastic zirconium alloy for living tissues according to claim 1.

3. An eyeglasses, having a frame made of the super-elastic zirconium alloy for living tissues according to claim 1.

4. The super-elastic zirconium alloy for living tissues according to claim 1, wherein the alloy exhibits a maximum recoverable strain higher than 5.0%.

* * * * *